United States Patent [19]

Sato et al.

[11] Patent Number: 4,632,907
[45] Date of Patent: Dec. 30, 1986

[54] PRESERVATIVE SOLUTION FOR FIXED AVIAN ERYTHROCYTES FOR THE VIRAL HEMAGGLUTINATION TEST

[75] Inventors: Akihiko Sato, Osaka; Kunihiro Nakajima, Nara, both of Japan

[73] Assignee: Shionogi & Co., Ltd., Osaka, Japan

[21] Appl. No.: 766,940

[22] Filed: Aug. 19, 1985

[30] Foreign Application Priority Data

Aug. 31, 1984 [JP] Japan .................. 59-183039

[51] Int. Cl.⁴ .......................................... G01N 31/00
[52] U.S. Cl. ...................... 436/10; 436/13; 436/15; 436/16; 436/18
[58] Field of Search ............ 436/8, 10, 15, 16, 18, 436/31

[56] References Cited

U.S. PATENT DOCUMENTS

| | | | |
|---|---|---|---|
| 3,640,896 | 2/1972 | De Casperis | 436/15 |
| 3,876,375 | 4/1975 | Maurukas | 436/15 |
| 3,920,580 | 11/1975 | Mast | 436/15 |
| 4,040,785 | 8/1977 | Kim et al. | 436/15 |
| 4,045,176 | 8/1977 | Proksch et al. | 436/15 |
| 4,121,905 | 10/1978 | Maurukas | 436/15 |
| 4,140,754 | 2/1979 | Iwasa | 436/10 |
| 4,189,401 | 2/1980 | Louderback | 436/15 |
| 4,302,355 | 11/1981 | Turner et al. | 436/10 |
| 4,324,687 | 4/1982 | Louderback et al. | 436/10 |

Primary Examiner—Richard D. Lovering
Assistant Examiner—T. J. Wallen
Attorney, Agent, or Firm—Birch, Stewart, Kolasch & Birch

[57] ABSTRACT

A preservative solution for fixed avian erythrocytes for the viral hemagglutination test of this invention comprises purified water which may contain serum albumin, glycerol or dimethyl sulfoxide and, additionally, a preventive against the growth of bacteria as occasion demands. Fixed avian erythrocytes can stably be preserved in this solution. HA and HI test can precisely be performed by employing fixed avian erythrocytes suspended in this invention.

4 Claims, 2 Drawing Figures

PRESERVATIVE SOLUTION FOR FIXED AVIAN ERYTHROCYTES FOR THE VIRAL HEMAGGLUTINATION TEST

BACKGROUND OF THE INVENTION (1) Field of the Invention

Some types of viruses carry on their surface a material called HA antigen (Hemagglutination antigen) which agglutinates animal erythrocytes. In hemagglutinatin of HA antigen it is well known that certain kinds of viruses agglutinaté erythrocytes of the same corresponding kinds of animals. For instance, a rubella virus agglutinates a one-day-old chick's erythrocytes as well as goose erythrocytes, an influenza virus agglutinates chicken erythrocytes (one-day-old and adult), a parainfluenza virus agglutinates guinea pig and chicken erythrocytes and a measles virus agglutinates monkey's erthrocytes. Accordingly, viruses can be identified and quantified by utilizing the above property.

The present invention relates to a preservative solution for fixed erythrocytes employed in a hemagglutination reaction (HA reaction) and a hemagglutination inhibition reaction (HI reaction) based upon the above hemagglutination of viruses. The HA and HI reactions have generally been utilized in diagnosing viral disease in the field of clinical testing.

(2) Description of the Prior Art

The HA reaction is employed in identifying a virus and determining its titer by utilizing the above specific antigenicity of several kinds of viruses. The HI reaction is utilized in determining an antibody against the HA antigen, that is which, HI antibody an organism acquires as a result of an immune response against a viral infection. Both reactions need erythrocytes as a reaction reagent. Though the use of fresh erythrocytes is preferable in order to make the agglutination or the agglutination inhibition reaction clear and accurate, this is practically impossible since it is not easy to get fresh erythrocytes on each test. Therefore, such a preservation method has been studied as the potency of erythrocyte for agglutination is not diminished even after longterm storage. For example, methods such as fixation with formalin etc., freeze-preserving or freeze-drying of fixed erythrocytes and so on are exemplified. In freeze-drying, further stabilization of erythrocyte has been attempted by such a treatment before the freeze-drying as washing which removes salt from the erythrocyte (JPN. Pat. NO. 50-37724), addition of glucose or serum albumin (JPN. Unexamd. Pat. Publn. No. 54-23119), and so on. However, a longterm preserving method for fixed erythrocytes in solution without freeze-drying has not yet been developed.

In developing a preservative solution able to keep erythrocytes stable for a long time without decreasing their ability to be agglutinated first we intended to elucidate the cause of nonspecific inhibition of the agglutination which restricts specific hemagglutination of rubella virus and consequently makes its result inaccurate. As a result, it was elucidated that the nonspecific inhibition of agglutination is caused by a phosphate buffer solution or a physiological salt solution which is usually used as a preservative solution for erythrocyte. Namely, the use of these solutions causes the exudation of $\beta$-lipoprotein from the fixed erythrocytes to nonspecifically inhibit hemagglutination. Therefore, if the fixed erythrocytes contain $\beta$-lipoprotein, in the rubella HI antibody titer test a negative specimen (antibody titer less than 8 times) may be misjudged as positive and accordingly the judgement by the test becomes impossible.

In general, erythrocytes fixed with aldehydes can be preserved for a long time. They are, however, destroyed by a mechanical stimulation such as shaking, mixing etc. and then $\beta$-lipoprotein exudes into an erythrocyte suspension. The reason why a lot of $\beta$-lipoprotein exudes is deduced that, where fixed erythrocytes are preserved in such a usual aqueous solution containing various salts such as physiological saline and the like, erythrocytes are strongly adhered to each other under the influence of the salts and consquently they must be placed in a mechanically more stimulated condition for a long time in order to efficiently disperse them before use.

SUMMARY

A preservative solution for fixed avian erythrocytes for the viral hemagglutination test of this invention comprises preserving fixed avian erythrocytes in purified water such as distilled water or ion-exchanged water. If necessary, serum albumin, glycerol or dimethyl sulfoxide may be added. Additionallly a preventative against the growth of bacteria (for example, sodium azide, thimerosal and the like) may be added if necessary.

Where fixed avian erythrocytes are preserved in the preservative solution of this invention, the erythrocytes are well dispersed and stable after longterm cold storage, the adhesion of the fixed erythrocytes to each other is restricted and the exudation of $\beta$-lipoprotein is inhibited. Therefore the agglutination pattern is accurate and clear so that the judgement of agglutination is easy. Since nonspecific inhibition of agglutination is restricted, precise HA titer and HI titer are given. This erythrocyte suspension provides a clear agglutination pattern in the HA reaction and the HI reaction of viruses such as the rubella virus, the Japanese encephalitis virus, the mumps virus and the like. Furthermore, the erythrocyte suspension does not alter after longterm storage in terms of the effect.

DETAILED DESCRIPTION OF THE INVENTION

Figure 1:
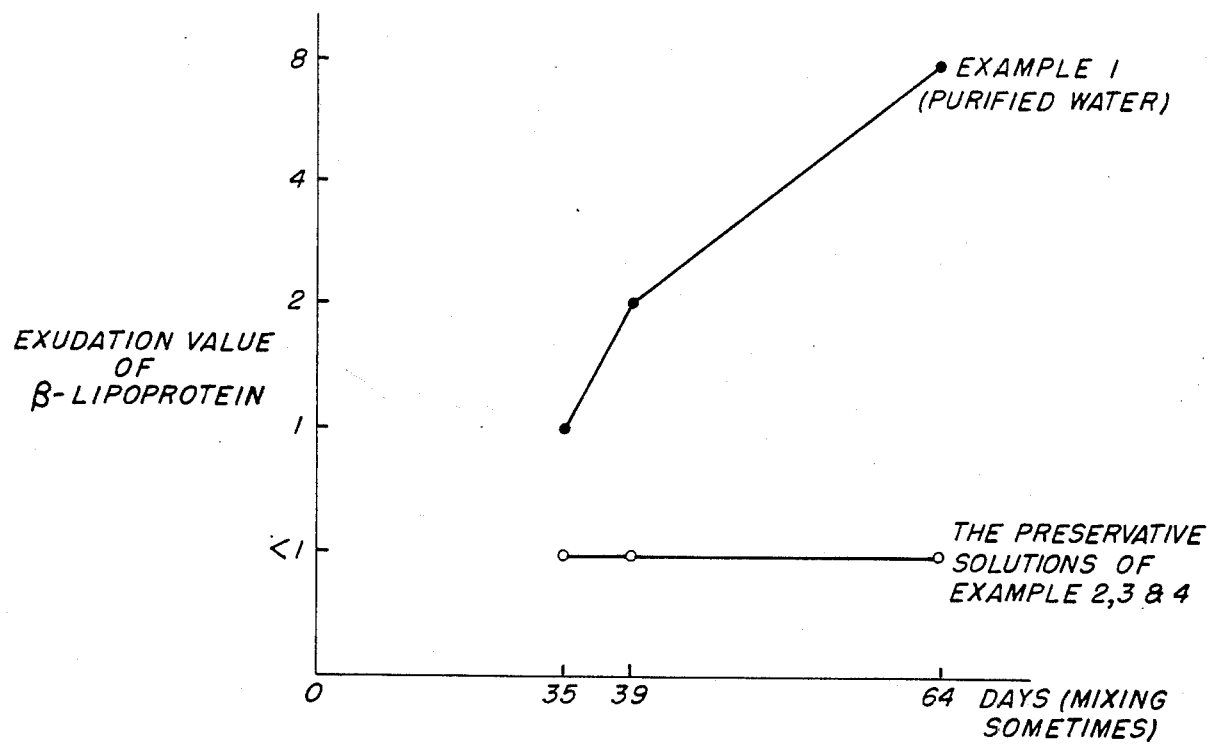
FIG. 1 shows a change on standing of the value of $\beta$-lipoprotein exuding in the erythrocyte suspension of example 1 and each erythrocyte suspension using the preservative solutions of examples 2, 3 and 4.

In order to prevent the above exudation of $\beta$-lipoprotein, therefore, it is necessary to suspend fixed erythrocytes in purified water and not in phosphate buffer solution or physiological saline, and the nonspecific inhibition of agglutinaion can be prevented by this method.

Moreover, it was recognized that erythrocytes become more stable by the addition of appropriate amount of serum albumin, glycerol or methylsulfoxide to this preservative solution consisting of comprising purified water and additionally, the addition of a preventative against the growth of bacteria which makes erythroyctes more durable for longterm storage.

The fixed erythrocytes preservable in the solution of this invention are of avain such as a goose, a chicken and the like, and especially the effect to goose erythrocytes is remarkable. Fixation is achieved according to usual methods by using a usual fixative such as formaldehyde, glutarardehyde and so on. For example, erythrocytes are fixed with about 0.1 to about 0.3% (V/V) solution of glutaraldehyde in about 1 to about 2 hours.

The preservative solution of this invention comprises purified water such as distilled water or ion-exchanged water.

As occasion demands, serum albumin, glycerol or dimethyl sulfoxide may be added. The serum albumin ia added in such a way as its concentration reaches about 0.01 to about 1.0% (W/V), preferably about 0.05 to about 0.2% (W/V). Serum albumin of human, bovine, horse, rabbit or the like can be employed and bovine serum albumin is more preferable. Glycerol or dimethyl sulfoxide may be added in such a way as the concentration reaches about 5 to about 10% (V/V).

Moreover, a preventive against the growth of bacteria (for example, sodium azide, thimerosal and the like) may be added as occasion demands, whose concentration may be as thick as prepared for the purpose of antisepsis, for example, about 0.01 to about 0.2% (W/V). Especially the use of sodium azide brings high stability.

HA test to virus, especially rubella virus, Japanese encephalitis virus, mumps virus, influenza virus and so on, and HI test for quantifying HI antibody in sera can be performed by employing the above avian erythrocytes suspended in the preservative solution of this invention.

Where fixed avian erythrocytes are suspended in the preservative solution of this invention up to the desired concentration, preferably about 8 to about 12% (V/V), the erythrocytes are well dispersed and stable after longterm cold storage. Therefore the agglutination pattern is accurate and clear and so the judgement of agglutination is easy. Since nonspecific inhibition of agglutination is restricted, precise HA titer and HI titer are given. This erythrocyte suspension provides clear agglutination pattern in HA reaction and HI reaction virus such as rubella virus, Japanese encephalitis virus, mumps virus and the like, especially in those of rubella virus, and does not alter after longterm storage in terms of the effect.

EXAMPLE

This invention is exemplified by the following examples but is not limited by these examples.

EXAMPLE 1

In purified water is dispersed 100 ml of fixed goose erythrocytes to give 10% erythrocyte suspension.

EXAMPLE 2

In purified water (total volume 1000 ml) are dissolved 1 g of bovine serum albumin and 1 g of sodium azide with stirring to be used for the preservation of fixed erythrocytes.

EXAMPLE 3-10

The following ingredients and purified water (total volume 1000 ml) are mixed in the same way as in example 2 to give a preservative solution.

TABLE 1

| Example | Ingredient | Amount | Conc. |
|---|---|---|---|
| 3 | glycerol | 100 ml | 10% (V/V) |
|   | sodium azide | 1 g | 0.1% (W/V) |
| 4 | dimethyl sulfoxide | 100 ml | 10% (V/V) |
|   | sodium azide | 1 g | 0.1% (W/V) |
| 5 | bonine serum albumin | 0.5 g | 0.05% (W/V) |
|   | sodium azide | 0.5 g | 0.05% (W/V) |
| 6 | glycerol | 40 ml | 4% (V/V) |
|   | sodium azide | 1 g | 0.1% (W/V) |
| 7 | horse serum albumin | 1 g | 0.1% (W/V) |
|   | sodium azide | 0.8 g | 0.08% (W/V) |
| 8 | horse serum albumin | 0.6 g | 0.06% (W/V) |
|   | thimerosal | 0.1 g | 0.01% (W/V) |
| 9 | glycerol | 80 ml | 8% (V/V) |
|   | thimerosal | 0.25 g | 0.025% (W/V) |
| 10 | dimethyl sulfoxide | 56 ml | 5.6% (V/V) |
|   | sodium azide | 1.2 g | 0.12% (W/V) |

EFFECT OF THE INVENTION (1) The fixed erythrocytes prepared in the following manner are suspended in the purified water of example 1 and the preservative solution of examples 2–4 to provide 10% suspensions, which are refrigerated with occasional stirring. The amount of exuded β-lipoprotein is quantified 35, 39 and 64 days later to give the result shown in FIG. 1. In these preservative solutions the exudation of β-lipoprotein was not recognized.

EXPERIMENT METHOD a. Preparation of Fixed Goose Erythrocytes

After goose erythrocytes obtained on the market are washed 3 times with physilogical saline and once with phosphate buffered saline (PBS) containing the following composition, they are suspended in the same PBS to provide about a 5% (V/V) suspension. To this erythrocyte suspension is added 1.5% glutaraldehyde solution diluted with PBS at a rate of 1 part by volume per nine parts by volume of erythrocytes and the mixture is allowed to react at room temperature for 60 minutes with moderate stirring by a stirrer. The resulting fixed erythrocytes are washed 6 times with purified water and suspended in a preservative solution.

| PBS: potassium chloride | 0.2 g |
|---|---|
| disodium hydrogenphosphate | 1.15 g |
| potassium hydrogenphosphate | 0.2 g |
| sodium chloride | 8.0 g |
| purified water up to | 1000 ml | b. Method of Quantification of Lipoprotein

Lipoprotein is quantified through the ability to inhibit the hemagglutination of rubella HA antigen. Namely, 0.5 ml of a preservative solution in which fixed erythrocytes are well dispersed are inoculated into a test tube and a centrifuged, and rubella HI test is performed with the resulting supernatant. In order to make the detection sensitivity of β-lipoprotein high, 2 units of rubella HA antigen are employed. The value of β-lipoprotein is defined as the frequency of maximum dilution which is able to inhibit the hemagglutination of the rubella virus. When the rubella HI test (according to the microplate method by the National Institute of Health, Tokyo, which comprises the use of VBS (Veronal buffer solution) containing BSA, gelatin, $Mg^+$ and $Ca^{2+}$ as a dilution solution and of goose or one-day-old chick erythrocytes. The general procedure is disclosed in Stewart et al, N. Engl. J. Med. 276,554 (1967), Halonen et al, Proc. Soc. Exp. Biol. Med. 125, 167 (1967) and so on.) is performed with erythrocytes which exude β-lipoprotein whose value was determined to be more than 8 times by this method, negative serum is judged as positive.

Figure 2:
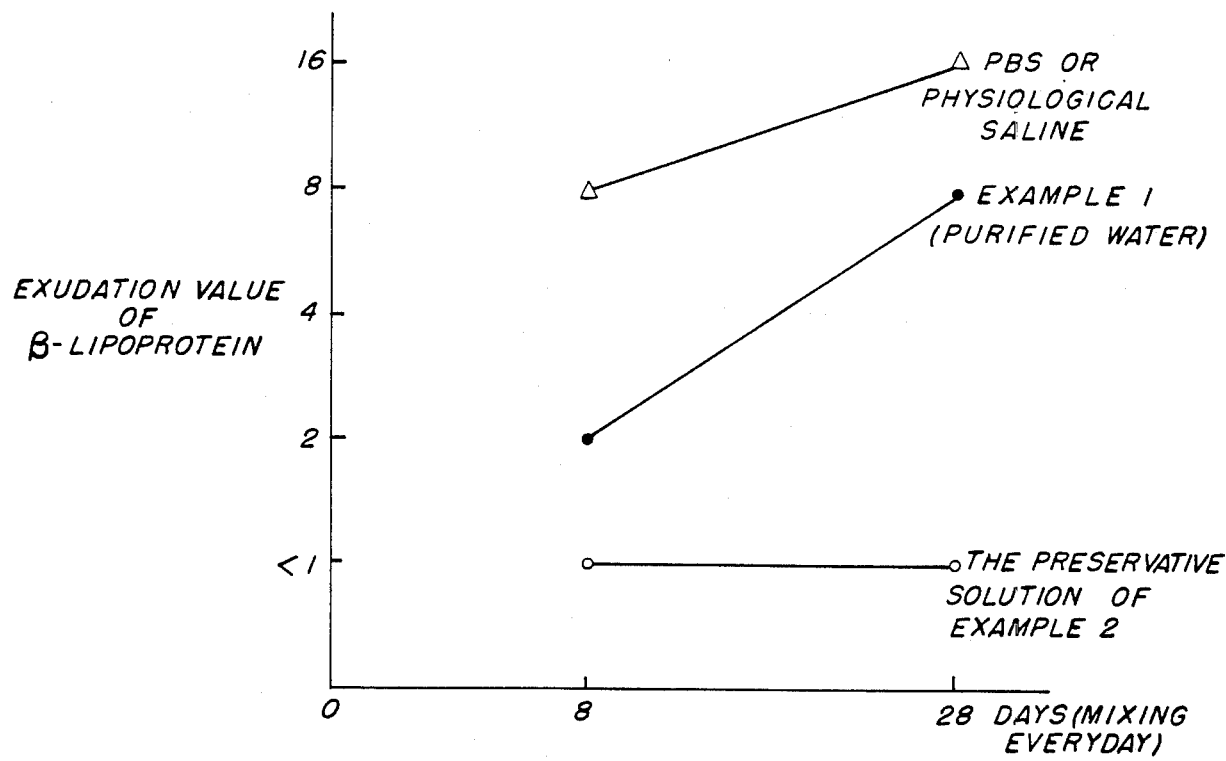
FIG. 2 shows a change on standing of the value of $\beta$-lipoprotein exuding in the erythrocyte suspension of example 1 and each erythrocyte suspension using the preservative solution of example 2, the phosphate buffered saline (PBS) and the physiological saline.

(2) The fixed goose erythrocytes noted in (1) is suspended in the preservative solution of example 2, PBS and physiological saline to give a 10% suspension. These suspensions and the suspension of example 1 are stored at 4°–10° C. with mixing once a day, the value of exuded β-lipoprotein is determined 8 and 28 days after. The result is shown in FIG. 2. β-lipoprotein exuding in the preservative solution of example 2 was not detected.

(3) Rubella HA (antigen titer) test and HI (antibody titer) test on 48 cylindrical patient serum specimens were performed by using fixed goose erythrocytes suspended in the preservative solution of example 2 and fresh erythrocytes suspended in DGV (dextrose gelatin veronal) buffer solution according to the microplate method by NIH, Tokyo. As shown in Tables 2 and 3, the results of the case using fixed goose erythrocytes suspended in the preservative solution of this invention and the case using fresh erythrocytes were exactly the same.

TABLE 2

Comparison of Rubella HA Antigen Titer

| Erythrocyte | Rubella HA Titer (Antigen Titer) |
| --- | --- |
| fixed erythrocyte | 64 |
| fresh erythrocyte | 64 |

TABLE 3

Comparison of Rubella HI Antibody Titer

Fixed erythrocyte in
the preservative solution
HI antibody titer

TABLE 3-continued

Comparison of Rubella HI Antibody Titer

| | <8 | 8 | 16 | 32 | 64 | 128 | 256 |
| --- | --- | --- | --- | --- | --- | --- | --- |
| 256 | | | | | | 1 | 3 |
| 128 | | | | | | 6 | 1 |
| 64 | | | | | 3 | | |
| 32 | | | | 7 | 1 | | |
| 16 | | 1 | 10 | 1 | | | |
| 8 | | 3 | | | | | |
| <8 | 11 | | | | | | |

HI antibody titer
Fresh erythrocyte in DGV buffer solution

What is claimed is:

1. A preservative solution of fixed avian erythrocytes for viral hemagglutination testing consisting essentially of:

about 8 to 12% (V/V) of fixed avian erythrocytes;
   about 0.01 to about 0.2% (W/V) of a preventative agent against the growth of bacteria selected from the group consisting of sodium azide and thimerosol;
   a stabilizer selected from the group consisting of 0.01 to about 1.0% (W/V) albumin, about 5 to 10% (V/V) glycerol and about 5 to 10% (V/V) dimethyl sulfoxide; and
   purified water selected from the group consisting of distilled water and ion-exhanged water.

2. A preservative solution for fixed avian erythrocytes useful for viral hemagglutination testing, consisting essentially of:

a preventative agent against the growth of bacteria selected from the group consisting of sodium azide and thimerosol;
   a stabilizer selected from the group consisting of albumin, glycerol and dimethyl sulfoxide; and
   purified water selected from the group consisting of distilled water and ion exchanged water.

3. The preservative solution of claim 2, further containing fixed avian erythrocytes.

4. The preservative solution of claim 2, which comprises:

about 0.01 to 0.2% (W/V) of the preventative agent; and
   a stabilizer selected from the group consisting of 0.01 to about 1.0% (W/V) albumin, about 5 10% (V/V) glycerol and about 5 to 10% (V/V) dimethyl sulfoxide.

* * * * *